United States Patent
Hsu

(10) Patent No.: US 10,143,477 B2
(45) Date of Patent: Dec. 4, 2018

(54) HEMOSTATIC EQUIPMENT

(71) Applicant: Cenefom Corp., Miaoli County (TW)

(72) Inventor: Chen-Ping Hsu, Miaoli County (TW)

(73) Assignee: CENEFOM CORP., Miaoli County (TW)

( * ) Notice: Subject to any disclaimer, the term of this patent is extended or adjusted under 35 U.S.C. 154(b) by 114 days.

(21) Appl. No.: 14/842,391

(22) Filed: Sep. 1, 2015

(65) Prior Publication Data

US 2016/0235953 A1 Aug. 18, 2016

(30) Foreign Application Priority Data

Feb. 16, 2015 (TW) .............................. 104105444 A

(51) Int. Cl.
| | | |
|---|---|---|
| *A61M 29/02* | (2006.01) | |
| *A61B 17/12* | (2006.01) | |
| *A61F 13/20* | (2006.01) | |
| *A61B 17/00* | (2006.01) | |

(52) U.S. Cl.
CPC .... *A61B 17/12104* (2013.01); *A61F 13/2005* (2013.01); *A61B 2017/00898* (2013.01)

(58) Field of Classification Search
CPC ......... A61B 17/24; A61B 2017/00898; A61M 29/02
See application file for complete search history.

(56) References Cited

U.S. PATENT DOCUMENTS

| | | | | | |
|---|---|---|---|---|---|
| 2,215,126 | A | * | 9/1940 | McMillin | A61B 17/12104 604/907 |
| 2,691,985 | A | * | 10/1954 | Newsom | A61B 17/12104 604/907 |
| 3,643,660 | A | * | 2/1972 | Hudson | A61M 16/0666 128/207.18 |
| 3,935,859 | A | * | 2/1976 | Doyle | A61F 5/08 606/196 |
| 4,338,941 | A | * | 7/1982 | Payton | A61B 17/12104 604/907 |
| 4,568,326 | A | * | 2/1986 | Rangaswamy | A61B 17/12022 604/1 |
| 4,950,280 | A | * | 8/1990 | Brennan | A61B 17/12022 604/1 |
| 5,584,822 | A | * | 12/1996 | Lively | A61B 17/12104 604/285 |
| 5,584,827 | A | * | 12/1996 | Korteweg | A61B 17/12022 604/11 |
| 7,294,138 | B2 | * | 11/2007 | Shippert | A61F 13/2005 604/104 |
| 2003/0105482 | A1 | * | 6/2003 | Hudson | A61B 17/1204 606/196 |
| 2013/0092173 | A1 | * | 4/2013 | Alexander | A61B 17/24 128/207.18 |
| 2013/0116656 | A1 | * | 5/2013 | Song | A61F 13/126 604/514 |

(Continued)

*Primary Examiner* — Julie A Szpira
(74) *Attorney, Agent, or Firm* — Chun-Ming Shih

(57) ABSTRACT

A hemostatic equipment has a pallet and an inflatable pillar. The pallet has a holder used for a patient to hold, providing foolproof effect in an operation direction to ensure that the inflatable pillar may enter a nasal cavity of a patient in a correct direction. The inflatable pillar has a head exposed with a pressing surface for pressing a bleeding site inside a nasal cavity of a patient to stop bleeding.

3 Claims, 18 Drawing Sheets

(56) References Cited

U.S. PATENT DOCUMENTS

| | | | |
|---|---|---|---|
| 2015/0017225 A1* | 1/2015 | Hubbell | A61L 15/64 424/444 |
| 2016/0030523 A1* | 2/2016 | Husain | A61K 38/363 128/200.14 |
| 2016/0256665 A1* | 9/2016 | Doshi | F16M 13/022 |

* cited by examiner

HEMOSTATIC EQUIPMENT

CROSS-REFERENCE TO RELATED APPLICATIONS

This application claims the priority of Republic of China Patent Application No. 104105444 filed on Feb. 16, 2015, in the State Intellectual Property Office of the R.O.C., the disclosure of which is incorporated herein by reference

BACKGROUND OF THE INVENTION

Field of the Invention

The invention relates to hemostatic equipment, specifically to hemostatic equipment capable of providing foolproof effect in an operation direction, and ease to use at home without assistance of professional medical staff.

Descriptions of the Related Art

Nasal hemorrhage is a symptom occurs occasionally in human nasal cavity. From statistics, nasal hemorrhage symptom occurs usually in the following groups: children with thinner nasal mucosa, elders with excessively dry nasal cavity due to few intranasal secretions, cardiovascular disease patients needing to take anticoagulant and patients with poor hypertension control. In addition, it also occurs usually for patients with nose injury and patients with postoperative hemorrhage in nose. The sites in the nasal cavity prone to bleeding are behind the junction of the nasal vestibule skin and the nasal mucosa. For current treatment with respect to nasal hemorrhage, people not only choose ice compress and local pressing to stop bleeding, but also choose to insert imbibition material into nasal cavity via nostril until proximity to the intranasal bleeding site. Thereby, the inflation due to absorption of intranasal blood compresses the intranasal bleeding site in order to mitigate intranasal hemorrhage symptom.

Generally, the patient with nasal hemorrhage would usually insert wadding composed of blood sucking material easily available at home, such as toilet paper, cotton, or gauze, into the nostril. However, such wadding tends to split under draw force, and is difficult for extraction from the nostril after blood sucking, or generates adhesion with inner wall of the nasal cavity in hemostasis process, such that secondary injury occurs for nasal cavity during extraction. Furthermore, there is risk of inhalation into nasal meatus or throat. Moreover, the most common problem occurs in that such wadding cannot press the bleeding site inside the nasal cavity of the patient in compliance with nasal cavity shape effectively, so that there is limited effect in mitigating intranasal bleeding symptom.

Therefore, someone designs nasal splint and nose stuffing cotton. The nasal splint is used to clip the nose. Generally, the nasal splint cannot clip the intranasal bleeding site exactly, so that intranasal bleeding symptom cannot be mitigated. The nose stuffing cotton can absorb liquid in the nasal cavity, and get inflated after absorbing the liquid to press the cavity wall of the nasal cavity. Before using the nose stuffing cotton, people usually need to apply force through fingertip to guide the nose stuffing cotton to enter inferior nasal meatus through nostril. However, people cannot view their own nasal meatus without other observation apparatus. Moreover, general people have no knowledge about channel of nasal meatus, together with fear about insertion of nose stuffing cotton into nostril, so that it is very difficult for the nose stuffing cotton to get close to the bleeding site inside the nasal cavity smoothly. Predictable effect for operation of nose stuffing cotton is available only with assistance from professional medical staff, so that it cannot be used by individually at home.

Thus, dealers in current medical field desires to develop a medical instrument by providing a hemostatic equipment for home use, such that a patient under hemorrhage symptom can operate to stop bleeding for the bleeding site inside the nasal cavity individually.

SUMMARY OF THE INVENTION

In view of the shortages of prior technologies mentioned above, the invention provides a hemostatic equipment for stopping bleeding inside a nasal cavity of a patient. The hemostatic equipment includes a pallet and at least one inflatable pillar. The pallet has a carrier and a holder, said holder extending downwards from a first end of said carrier for the patient to hold, the holder may be applied a force to move the carrier toward a nostril of the patient. The inflatable pillar has a head and a body. The head is exposed with a pressing surface for pressing a bleeding site inside the nasal cavity of the patient as inflated. A tail end of the body is implanted onto a second end of the carrier.

Optionally, the inflatable pillar can be compressed in forming for the head to enter the nasal cavity of the patient smoothly as uninflated. The head is larger than the body with respect to the compression rate in forming, such that lateral figure of the inflatable pillar is approximate to a "1" shape as uninflated. The carrier may have multiple walls to define an implantation area for implanting the tail end of the inflatable pillar. Perfectly, a distance length between the left and right boundaries of the implantation area is larger than a width length of the inflatable pillar.

Optionally, the provided hemostatic equipment may comprise two inflatable pillars which are arranged separately and can respectively enter left and right nostrils of the patient smoothly in use. A second end of the carrier has a disconnection slot extended from an outer edge inwards to define a left cantilever and a right cantilever, and the two inflatable pillars are arranged on the left cantilever and the right cantilever, respectively. The pallet has a weakness for separating the left cantilever and the right cantilever. The carrier has a bore for the apex nasi of the patient to enter in use, and the bore is formed on an extended tail end of the disconnection slot. The holder has defined a finger-through space below the carrier for the patient to operate the holder with fingers.

Optionally, the inflatable pillar is made of a porous foam material. Perfectly, the inflatable pillar is made of a foam material containing polyvinyl alcohol. The pallet is made of a plastic material. The inflatable pillar may be filled with a medicine for treating bleeding inside the nasal cavity of the patient. The inflatable pillar comprises a through-hole having openings on the head and the body, respectively, the carrier being formed with a hole in communication with the through-hole.

Optionally, the provided hemostatic equipment may have a test strip contacted the inflatable pillar for testing the state of the inflatable pillar. Lateral figure of the inflatable pillar as inflated is approximate to inverted L shape or T shape so that it can press the bleeding site inside the nasal cavity of the patient.

Moreover, the inflatable pillar may also utilize the head to engage inside the nasal cavity of the patient as inflated, such that easy detachment from nostril during use is avoided. The holder is intersected with the carrier vertically. The pallet has a reinforcement body arranged at intersection of the carrier and the holder. The inflatable pillar can be implanted onto the carrier in sticking, locking, injection combination or engagement.

In comparison with prior arts, a hemostatic equipment of the invention has a holder for a patient to hold, providing foolproof effect in operation. The holder ensures that an inflatable material used for hemostasis enters a nasal cavity of a patient in a correct direction, and then presses the bleeding site inside the nasal cavity of the patient directly, such that bleeding inside the nasal cavity of the patient is stopped after inflation of the inflatable material. Therefore, it may be operated by oneself and is applicable to home treatment.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
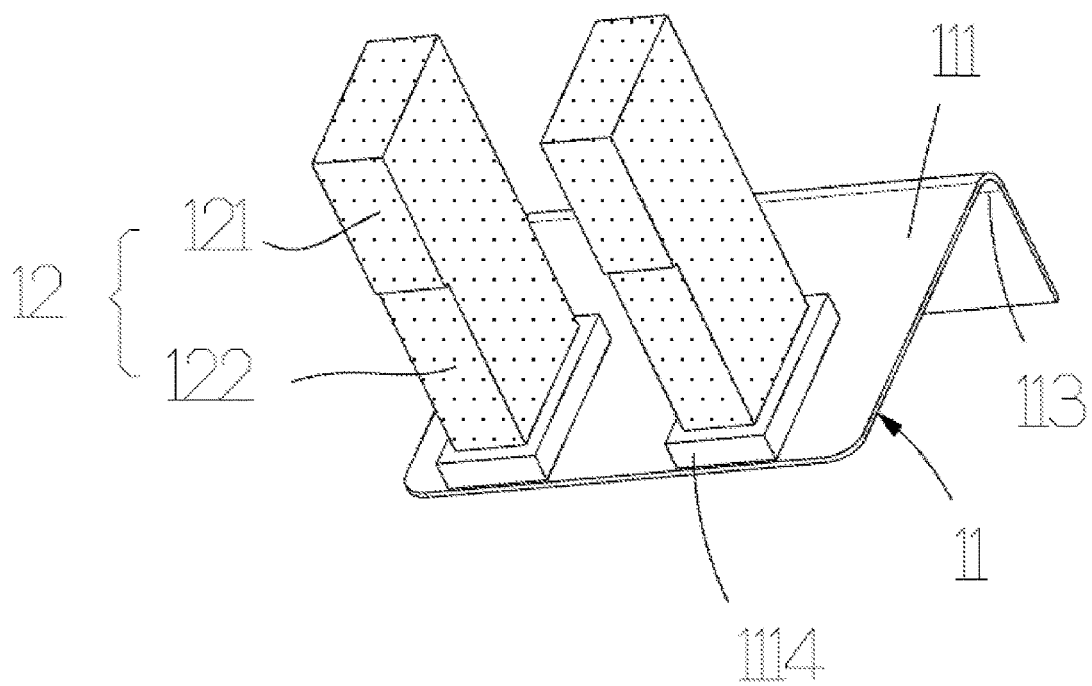
FIG. 1 is a schematic diagram showing a first state of a first example of a hemostatic equipment according to the invention, wherein an inflatable pillar is not in inflation.

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

The invention provides a hemostatic equipment for stopping bleeding inside a nasal cavity of a patient. It is advantageous of ease to use that the patient can operate individually without assistance from professional medical staff to achieve hemostasis for a bleeding site inside the nasal cavity, and it may be used by people at home to stop nasal hemorrhage not relative to surgery. Specifically, it may be used to improve nasal hemorrhage symptom of children with thinner nasal mucosa, elders with excessively dry nasal cavity due to few intranasal secretions, cardiovascular disease patients needing to take anticoagulant and patients with poor hypertension control. Furthermore, it may also be used to improve nasal hemorrhage symptom of patients with injured nose and patients with postoperative hemorrhage in nose.

Several technologically representative examples of the invention are recited below. In order to simplify the disclosure of the invention, in each of the recited examples, the same or like elements are illustrated with the same symbol and the same or like illustrations are done in simplified modes.

FIRST EXAMPLE

Refer to FIG. 1 to FIG. 5, in which a schematic diagram for a first example of the hemostatic equipment of the invention is shown. As shown in FIG. 1, the hemostatic equipment 1 of the invention is composed of at least a pallet 11 and an inflatable pillar 12. The pallet 11 has a carrier 111 and a holder 112, wherein the carrier 111 and the holder 112 may be made of plastic material. A patient may hold the pallet 11 by the holder 112, while a force is applied for the holder 112 to move the carrier 111 toward to a nostril of a patient. In the example, the holder 112 extends downwards from one end of the carrier 111 to define a finger-through space below the carrier 111. The finger-through space is for the patient to operate the holder 112 through fingers.

In the example, the holder 112 is intersected with the carrier 111 vertically, but not limited thereto. Intersection angle of the holder 112 and the carrier 111 may also be changed for a patient to operate the holder 112 easily, and even more, the holder 112 and carrier 111 may be set in one plane.

The inflatable pillar 12 may be made of porous foaming material. In forming, the inflatable pillar 12 may be compressed to shrink volume in order to enter the nasal cavity of a patient smoothly, and the inflatable pillar 12 may be inflated to press bleeding inside a nasal cavity of a patient to stop bleeding after absorbing liquid. The inflatable pillar 12 may be made of a material with good liquid absorption and inflation capabilities. Preferably, the inflatable pillar 12 may be made of foam material containing polyvinyl alcohol (PVA). Additionally, the inflatable pillar 12 shown in FIG. 1 has a rectangular section, but shape of a section for the inflatable pillar 12 may also be changed to circle, ellipse, triangle or a combination of various shapes under different use circumstances.

The inflatable pillar 12 may be divided into two parts, a head 121 and a body 122. The head 121 is exposed with a pressing surface used to press a bleeding site inside a nasal cavity of a patient for hemostasis. Tail end of the body 122 is implanted on the carrier 111 away from the holder 112. Preferably, the carrier 111 may have multiple walls 1114 to define an implantation area used for implanting tail end of the body 122 of the inflatable pillar 12, beneficial to implantation of the inflatable pillar 12. Moreover, each of the walls 1114 may support tail end of the body 122 of the inflatable pillar 12 laterally to assure the inflatable pillar 12 on the carrier 111.

For the inflatable pillar 12 with respect to the compression rate in forming, the head 121 is larger than the body 122 such that the head 121 may enter a nasal cavity of a patient through a nasal meatus of a patient smoothly before inflation of the inflatable pillar 12. As shown in FIG. 1, lateral figure of the inflatable pillar 12 is approximate to a "1" shape before inflation of the inflatable pillar 12, that is the section size of the head 121 is close to that of the body 122, such that the head 121 may enter the nasal cavity of the patient smoothly before inflation of the inflatable pillar 12.

Figure 4:
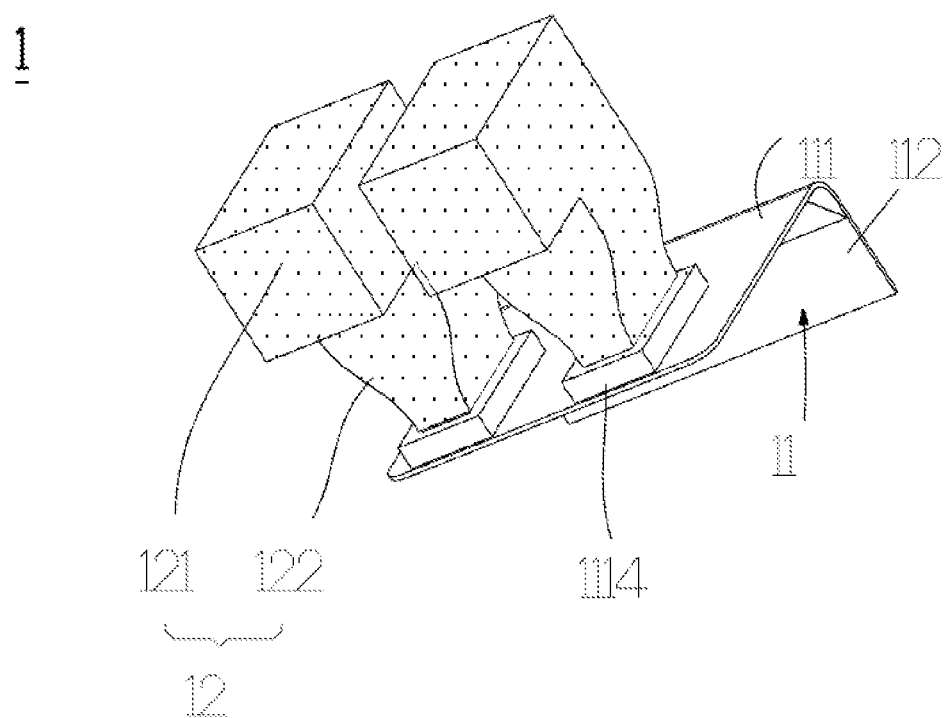
FIG. 4 is a schematic diagram showing a second state of a first example of a hemostatic equipment according to the invention, wherein an inflatable pillar is in an inflation state.

As the inflatable pillar 12 absorbs blood, the inflatable pillar 12 is in inflation, and the volume of the head 121 is larger than that of the body 122, such that the pressing surface of the head 121 may move until pressing a bleeding site inside of a nasal cavity of a patient. As shown in FIG. 4, the inflatable pillar 12 is in inflation, wherein section size of the head 121 is larger than that of the body 122 apparently, and the head 121 is inflated in a specific direction. In such state, lateral figure of the inflatable pillar 12 is approximate to inverted L shape, or approximate to T shape such that the head 121 is available to press a bleeding site inside of a nasal cavity of a patient, and may be engaged inside a nasal cavity of a patient for pressing continuously. In addition, the inflatable pillar may utilize the head engaged inside a nasal cavity of a patient to avoid easy detachment from a nostril of a patient during use to provide continuous hemostatic function.

The inflatable pillar 12 may be implanted onto the carrier 111 in at least one mode of sticking, locking and engagement, but not limited thereto. Other modes are available, such as direct combination with the inflatable pillar 12 during injection molding of the carrier 111 to achieve implantation of the inflatable pillar 12 onto the carrier 111. The inflatable pillar 12 may be filled with a medicine for treating bleeding inside a nasal cavity of a patient such that the medicine is released from the inflatable pillar 12 after the inflatable pillar 12 enters the nasal cavity to accelerate treatment of intranasal bleeding symptom.

Figure 2:
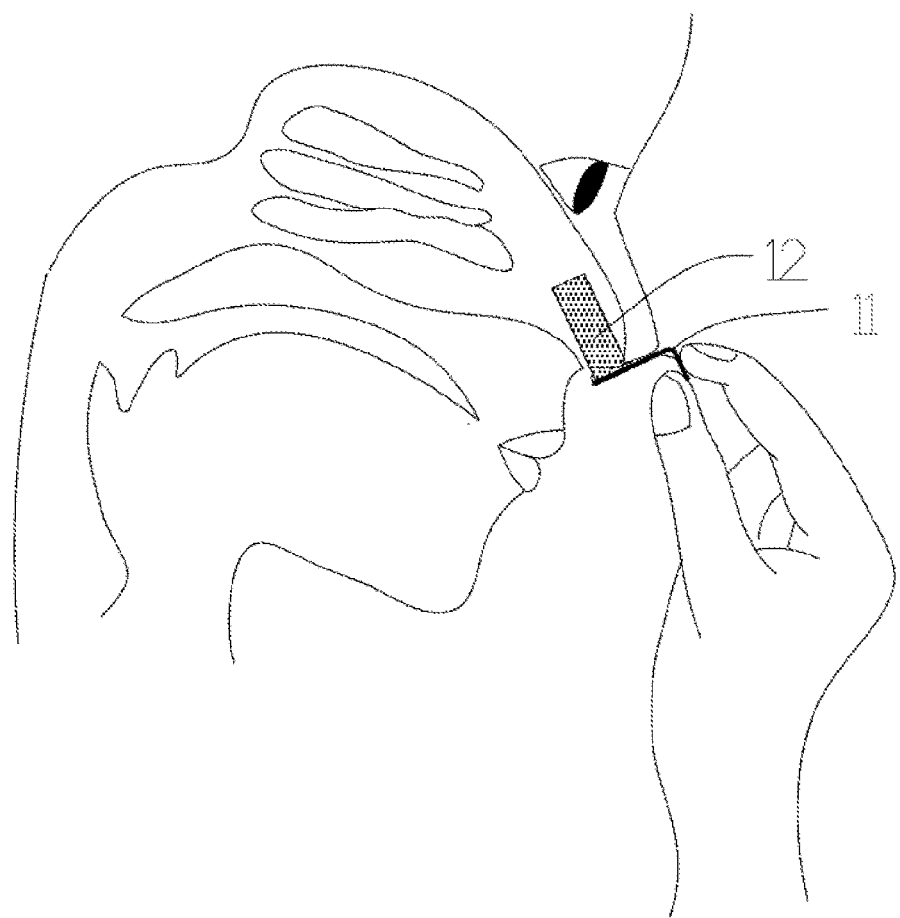
FIG. 2 is a schematic diagram showing a first use state of the hemostatic equipment shown in FIG. 1, wherein the hemostatic equipment is in a correct operation direction and can enter a nostril of a patient.
Figure 5:
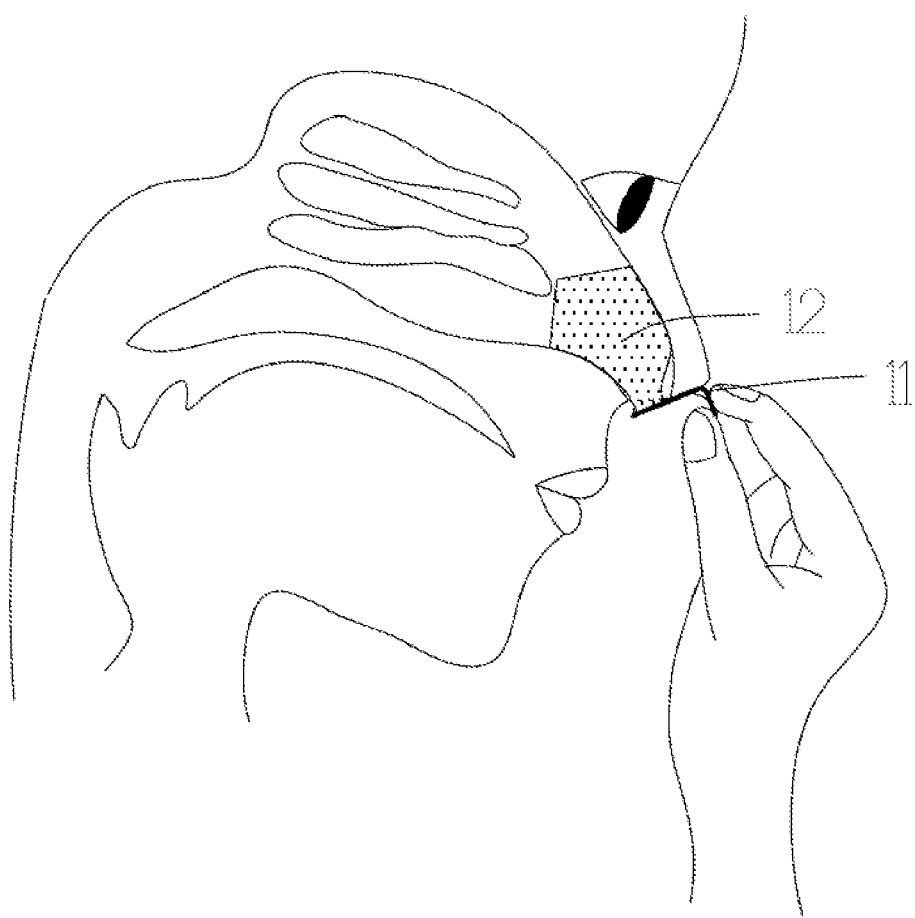
FIG. 5 is a schematic diagram showing a use state of the hemostatic equipment shown in FIG. 4.

The operation for the hemostatic equipment of the invention is directionality. As shown in FIG. 2, the hemostatic equipment 1 is operated in a correct direction (i.e., the direction for the pressing surface of the head 121 is correct so that a bleeding site inside of a nasal cavity of a patient can be pressed by the pressing surface after inflation of the head 121). In such operation state, partial fingers of the patient for operation of the hemostatic equipment 1 may be stuck into the finger-through space below the carrier 111, and may abut outer wall of the holder 112 in conjunction with other fingers, respectively, in order to apply a force to the holder 112 to move the inflatable pillar 12 into the nasal cavity of the patient until the pressing surface of the head 121 of the inflatable pillar 12 is in alignment with a bleeding site inside a nasal cavity of a patient. Subsequently, as shown in FIG. 5, the inflatable pillar 12 entering the nasal cavity would get inflated after liquid absorption, such that the pressing surface of the head 121 is forced to press a bleeding site inside a nasal cavity of a patient for hemostasis.

Figure 3:
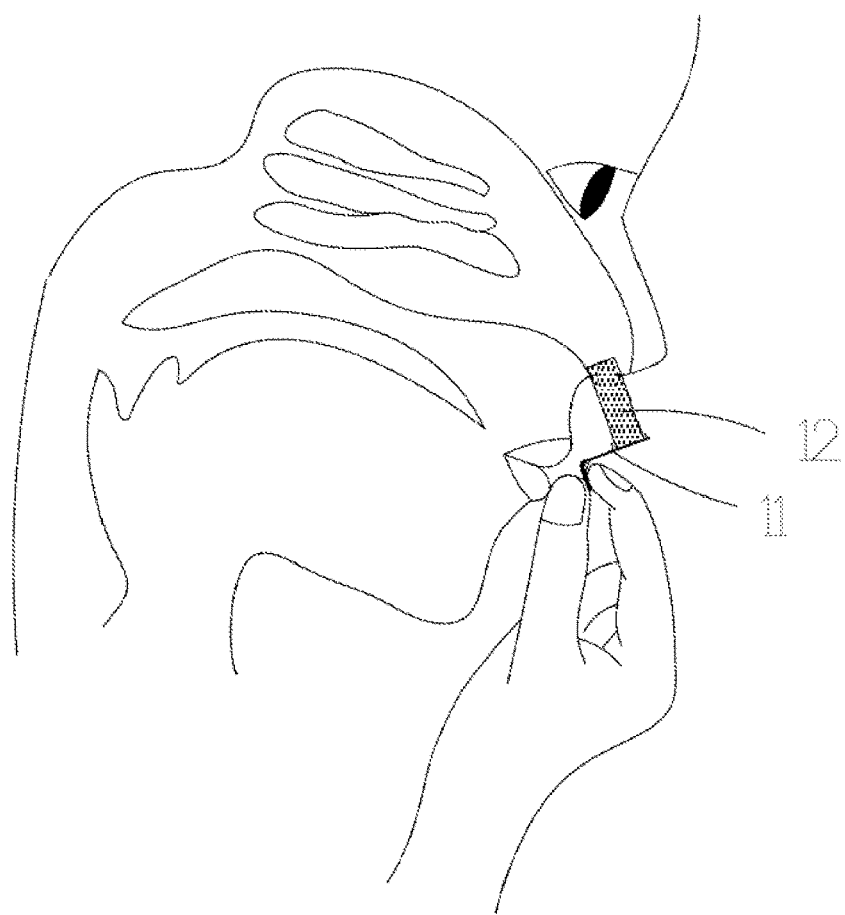
FIG. 3 is a schematic diagram showing a second use state of the hemostatic equipment shown in FIG. 1, wherein the hemostatic equipment is in a wrong operation direction and cannot enter a nostril of a patient.

As shown in FIG. 3, the hemostatic equipment 1 is operated in a wrong direction (i.e., the direction for the pressing surface of the head 121 is wrong, such that a bleeding site inside a nasal cavity of a patient cannot be pressed after inflation of the head 121). In such a state, in the process forcing movement of the inflatable pillar 12 with fingers of the patient that abut the holder 112, the fingers would touch a face of a patient and the inflatable pillar 12 is blocked from sticking into the nasal cavity of the patient. That is, the holder 112 may provide foolproof effect in operation direction to ensure that the pressing surface of the head 121 of the inflatable pillar 12 can enter a nasal cavity of a patient in a correct direction.

Therefore, the operation of the hemostatic equipment of the invention is directionality. As long as a patient operates the hemostatic equipment in a correct direction, the pressing surface of the head of the inflatable pillar may be in alignment with a bleeding site inside a nasal cavity of a patient, so that a patient can operate the hemostatic equipment of the invention by oneself without assistance from professional medical staff, suitable for home medical care. That is, the hemostatic equipment of the invention may provide foolproof effect in an operation direction, and ease to use at home without assistance from professional medical staff.

The hemostatic equipment disclosed in the example comprises two inflatable pillars 12 which are arranged separately on the carrier 111. The two inflatable pillars 12 can enter left and right nostrils of a patient, respectively. Distance between the two inflatable pillars 12 is defined by thickness of a nasal septum of a patient, such that the two inflatable pillars 12 can keep away from a nasal septum of a patient in use.

Additionally, in the example, the pallet 11 has a reinforcement body 113, which is arranged at intersection of the carrier 111 and the holder 112 to ensure that the carrier 111 and the holder 112 can keep combination under force application in operation, that is, the carrier 111 and the holder 112 would not separate due to force application easily in using the pallet 11.

SECOND EXAMPLE

Figure 6:
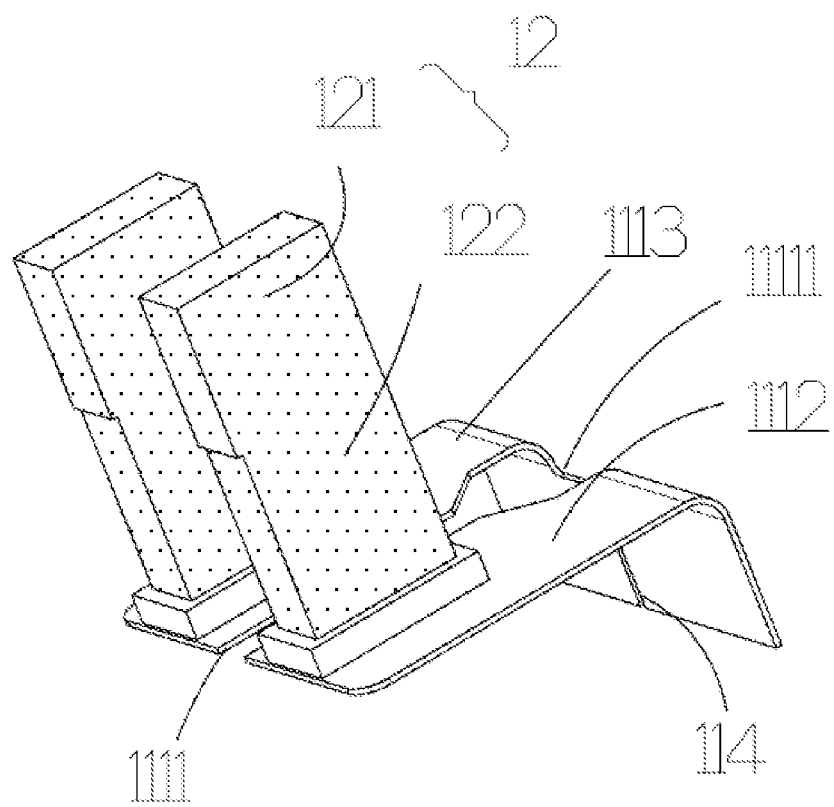
FIG. 6 is a schematic diagram showing a second example of a hemostatic equipment according to the invention, wherein a reinforcement body is arranged at an intersection of a holder and a carrier, and a carrier is arranged with a disconnection slot.

Refer to FIG. 6 showing a schematic diagram of a second example for the hemostatic equipment of the invention. The largest difference between the example and the above example is that: one end of the carrier 111 arranged with the inflatable pillar 12 has a disconnection slot 1111 extended from an outer edge inwards to define a left cantilever 1112 and a right cantilever 1113, which may be forced to deform, respectively, on the carrier 111. As shown in FIG. 6, the two inflatable pillars 12 are arranged on the left cantilever 1112 and the right cantilever 1113, respectively. The two inflatable pillars 12 can be moved by deformation of the left cantilever 1112 and the right cantilever 1113 to help to entering in a nasal cavity of a patient. The carrier 111 may be formed with a bore 11111 additionally for an apex nasi of a patient to enter when the hemostatic equipment 1 is in use, in order to prevent protruded portion of an apex nasi of a patient to abut the carrier 111, such that the head 121 of the inflatable pillar 12 can go deep into the nasal cavity of the patient. Preferably, the bore 11111 is formed on tail end of the disconnection slot 1111.

Additionally, in the hemostatic equipment of the example, the pallet 11 has a weakness 114 formed of structural weakness. A patient can separate the left cantilever 1112 and the right cantilever 1113 by fracturing the weakness 114, so that hemostasis for stopping bleeding inside a nasal cavity of a patient is available by using the inflatable pillar 12 of either the left cantilever 1112 or the right cantilever 1113.

THIRD EXAMPLE

Figure 7:
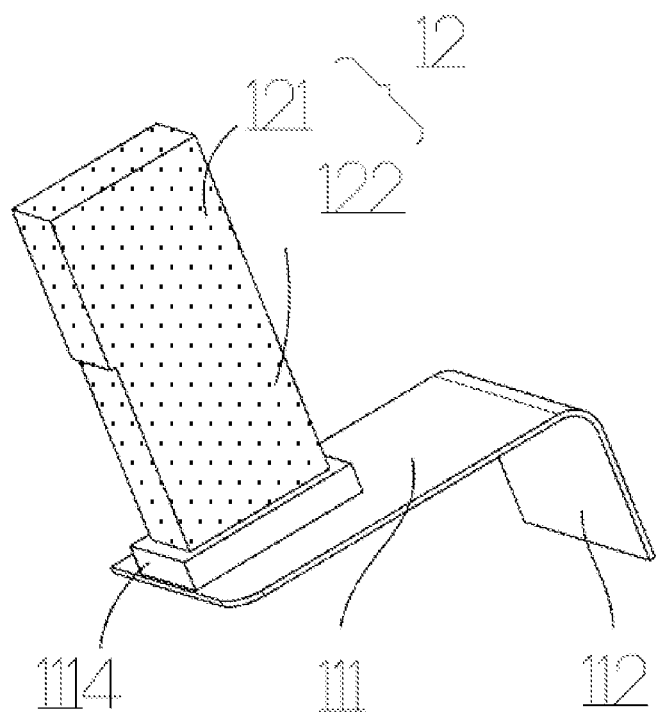
FIG. 7 is a schematic diagram showing a third example of a hemostatic equipment according to the invention, wherein only a single inflatable pillar is arranged on a carrier.
Figure 8:
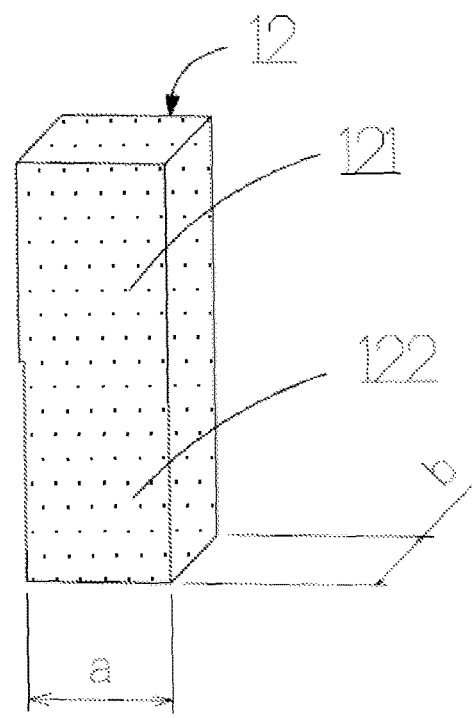
FIG. 8 is a schematic diagram showing a state of an inflatable pillar of a hemostatic equipment according to the invention before inflation.
Figure 9:
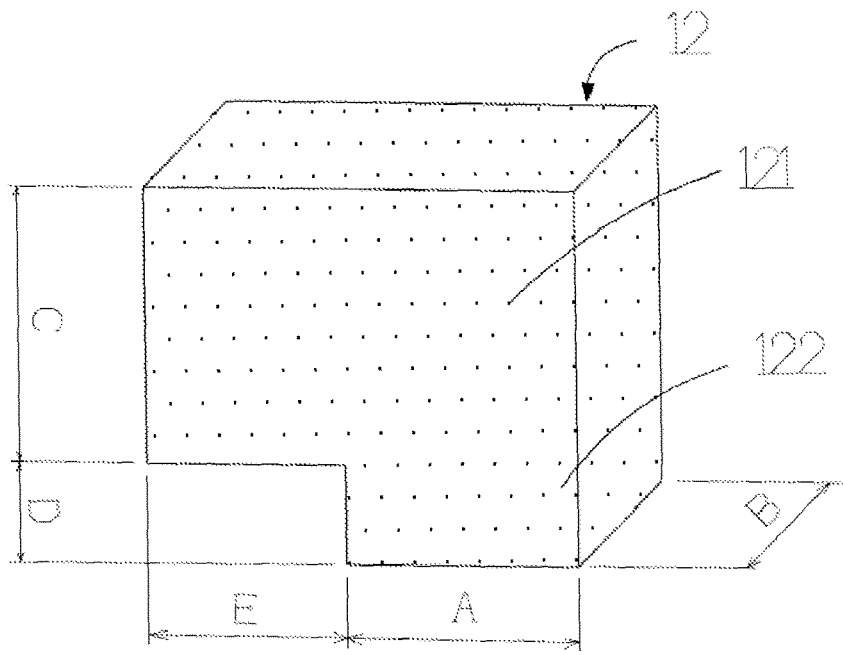
FIG. 9 is a schematic diagram showing a state of an inflatable pillar of a hemostatic equipment according to the invention after inflation.

Refer to FIGS. 7 to 9 showing schematic diagrams of the third example for the hemostatic equipment of the invention. The largest difference between the example and the above example is that: only one inflatable pillar 12 is arranged on the carrier 111 for hemostasis of a nostril of a patient in bleeding. Therefore, the number of the inflatable pillars arranged on the hemostatic equipment of the invention is not limited to two.

For applicability to users of various somatotypes, the size ranges of various lengths for the states of the inflatable pillar of the hemostatic equipment of the invention before and after inflation are illustrated as following: As shown in FIG. 8, the inflatable pillar 12 of the invention is in a state before inflation, wherein the length size indicated by symbol a is between 2.5 mm and 20 mm; the length size indicated by symbol b is between 1.5 mm and 15 mm. In addition, as shown in FIG. 9, the inflatable pillar 12 of the invention is in a state after inflation, wherein the length size indicated by symbol A is between 5 mm and 30 mm; the length size indicated by symbol B is between 3 mm and 22 mm; the length size indicated by symbol C is between 3 mm and 22 mm; the length size indicated by symbol D is between 1.5 mm and 7 mm; the length size indicated by symbol E is between 2 mm and 12 mm.

FOURTH EXAMPLE

Figure 10:
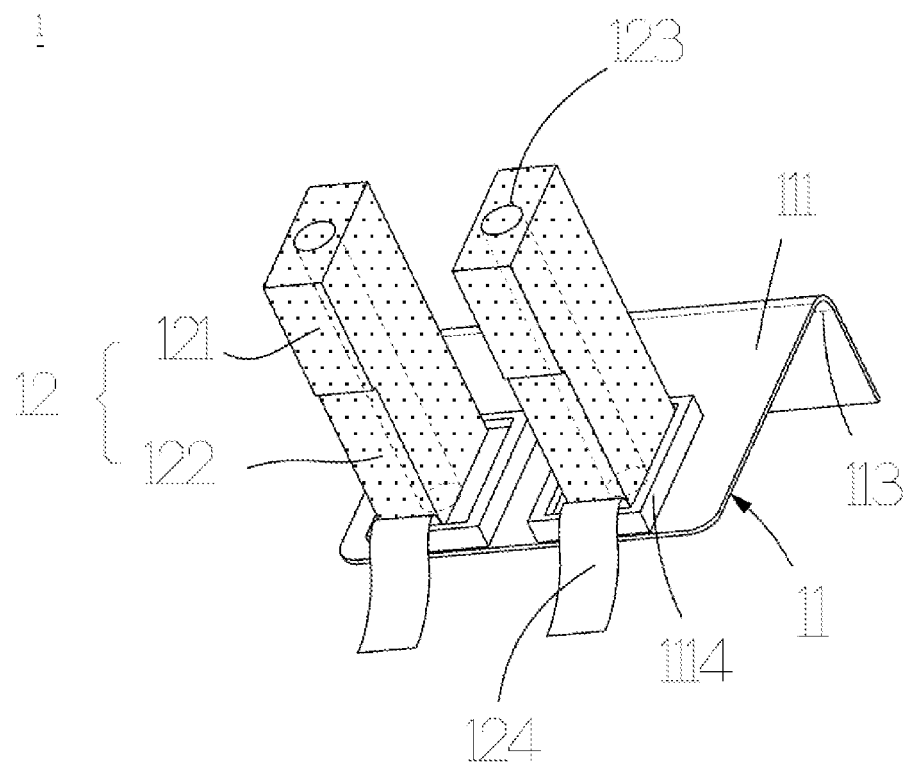
FIG. 10 is a schematic diagram showing a fourth example of a hemostatic equipment according to the invention.
Figure 11:
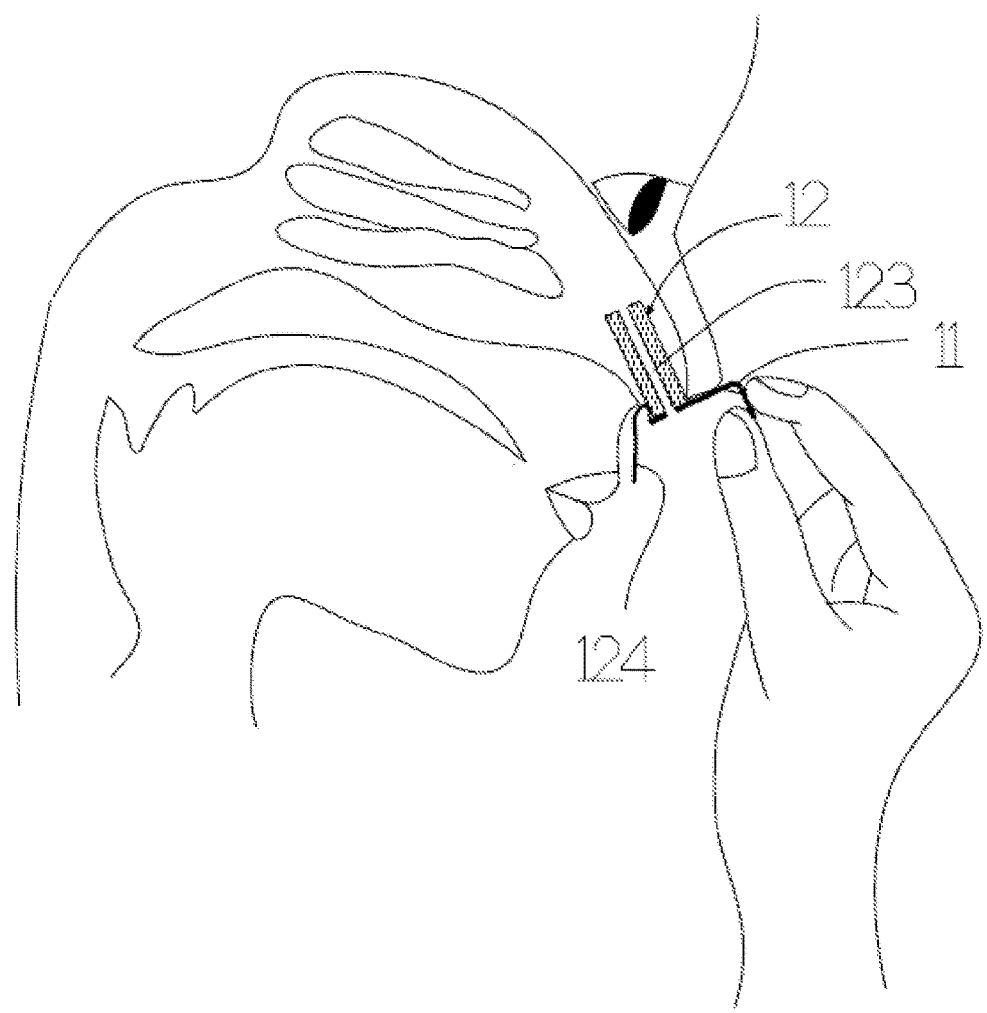
FIG. 11 is a schematic diagram showing a non-inflation state of an inflatable pillar of the hemostatic equipment shown in FIG. 10 after entering a nostril of a patient.
Figure 12:
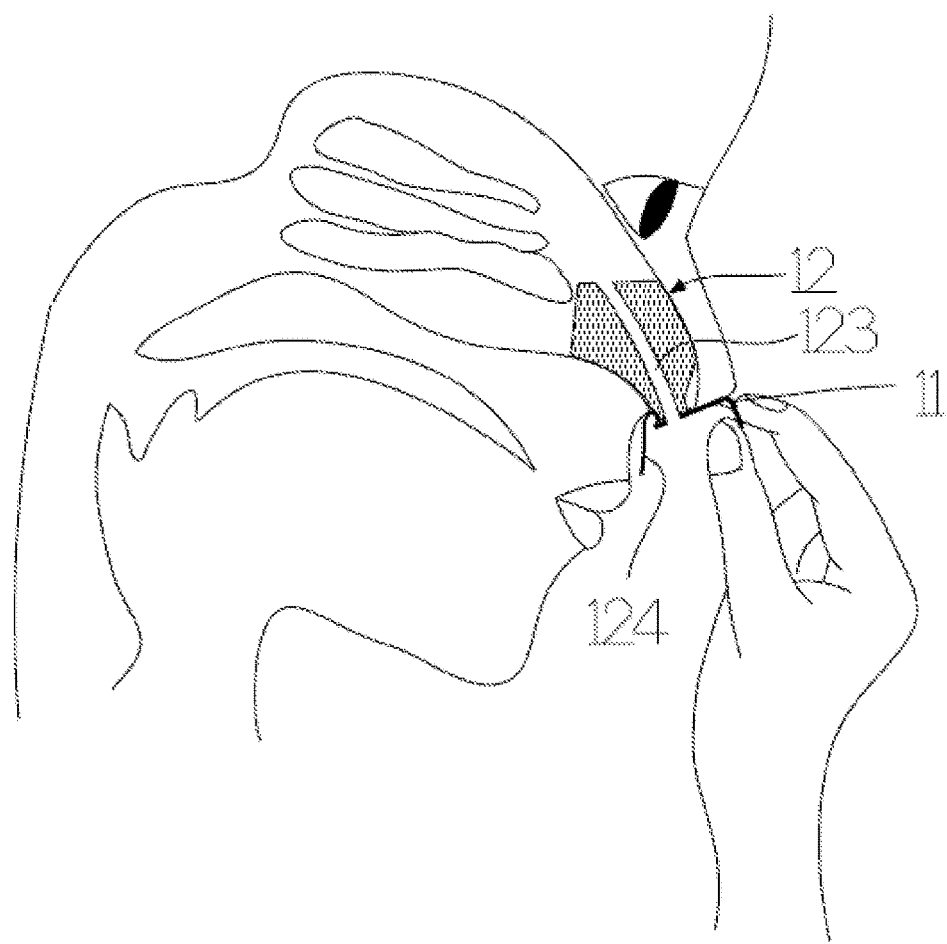
FIG. 12 is a schematic diagram showing an inflation state of an inflatable pillar of the hemostatic equipment shown in FIG. 10 after entering a nostril of a patient.

Refer to FIGS. 10 to 15 showing schematic diagrams of the fourth example for the hemostatic equipment of the invention. As shown in FIG. 10, an implantation area of the wall 1114 is formed on the pallet 11. As shown in FIG. 11, the inflatable pillar 12 can enter a nasal cavity of a patient before inflation smoothly. As shown in FIG. 12, the inflatable pillar 12 can press a bleeding site inside a nasal cavity of a patient to stop bleeding inside a nasal cavity of a patient after inflation.

Figure 13:
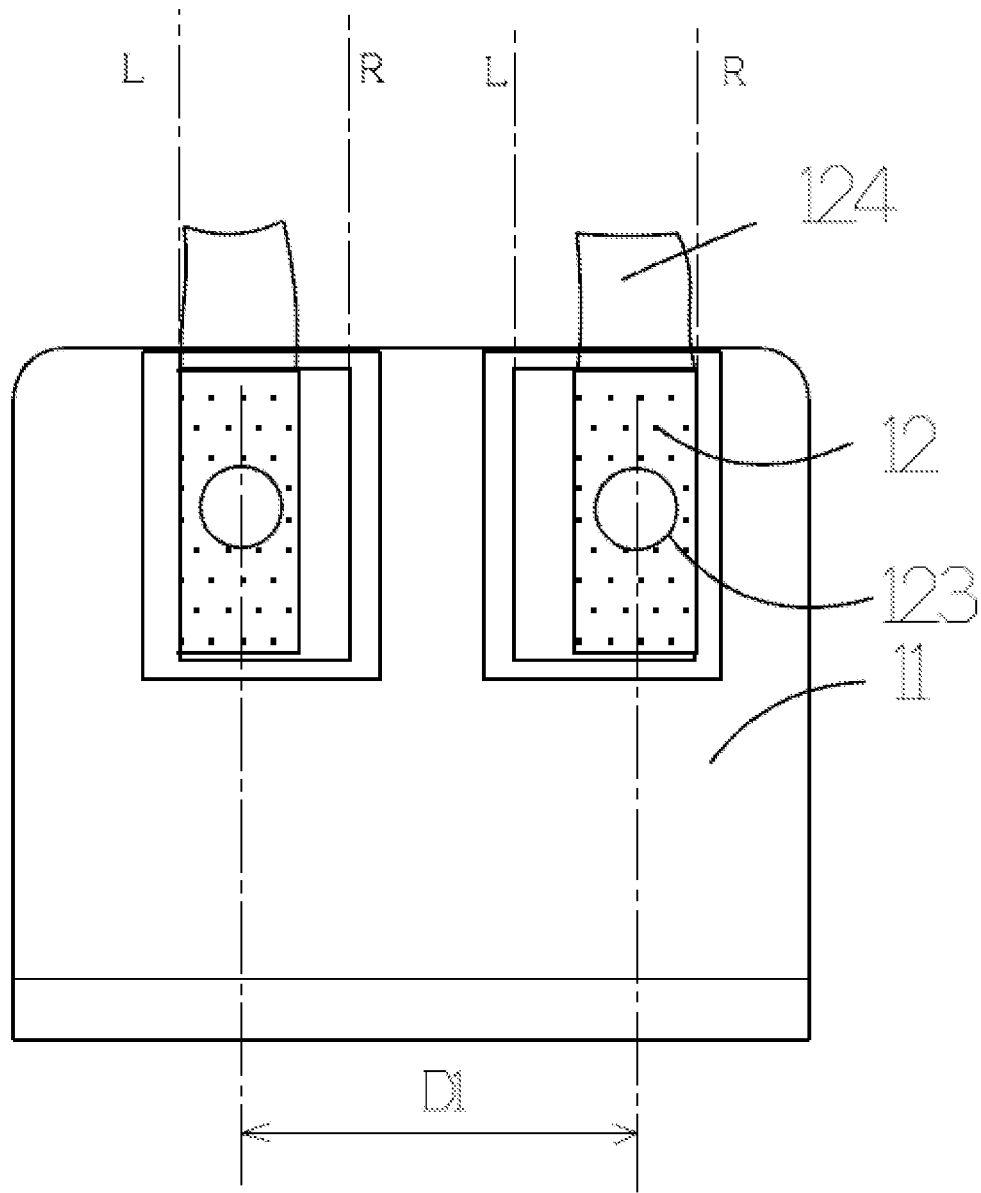
FIG. 13 is a top view showing the inflatable pillar in the fourth example of a hemostatic equipment according to the invention placed in a first mode.
Figure 14:
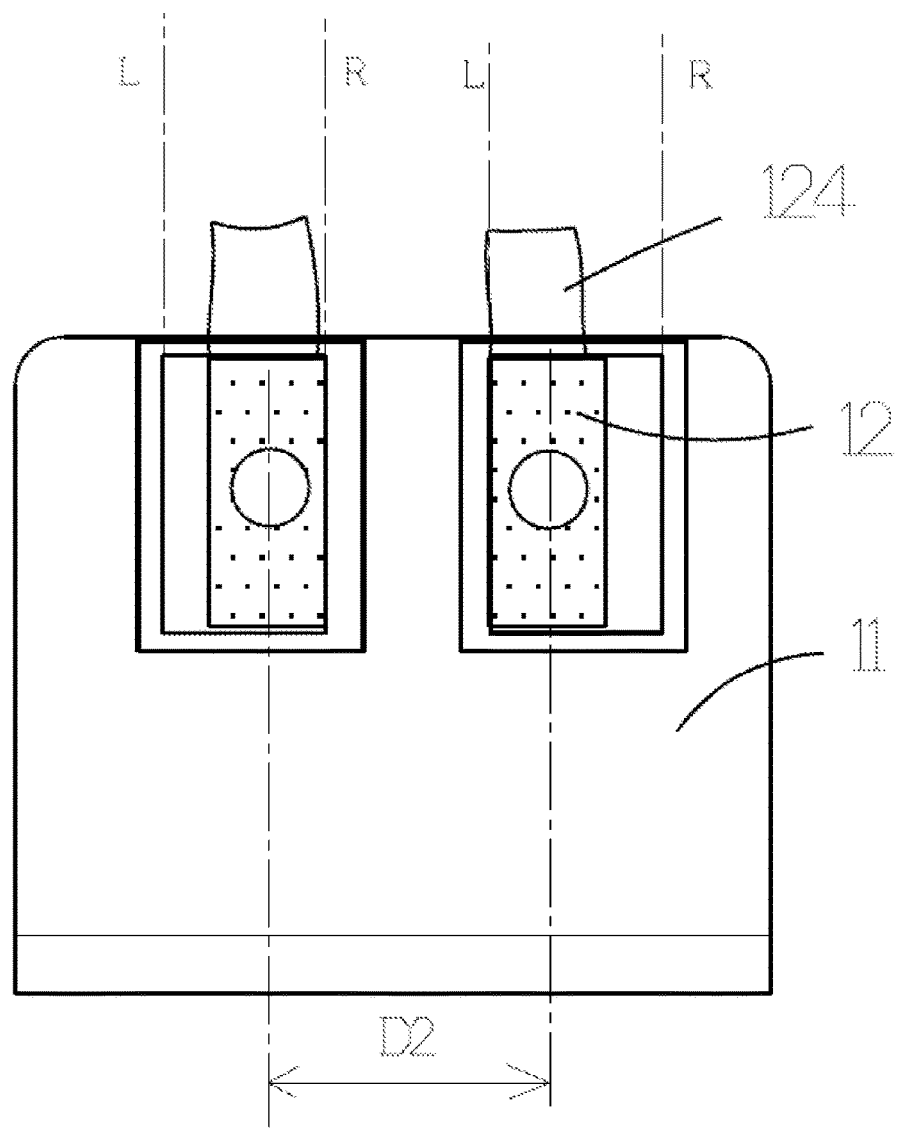
FIG. 14 is a top view showing the inflatable pillar in the fourth example of a hemostatic equipment according to the invention placed in a second mode.
Figure 15:
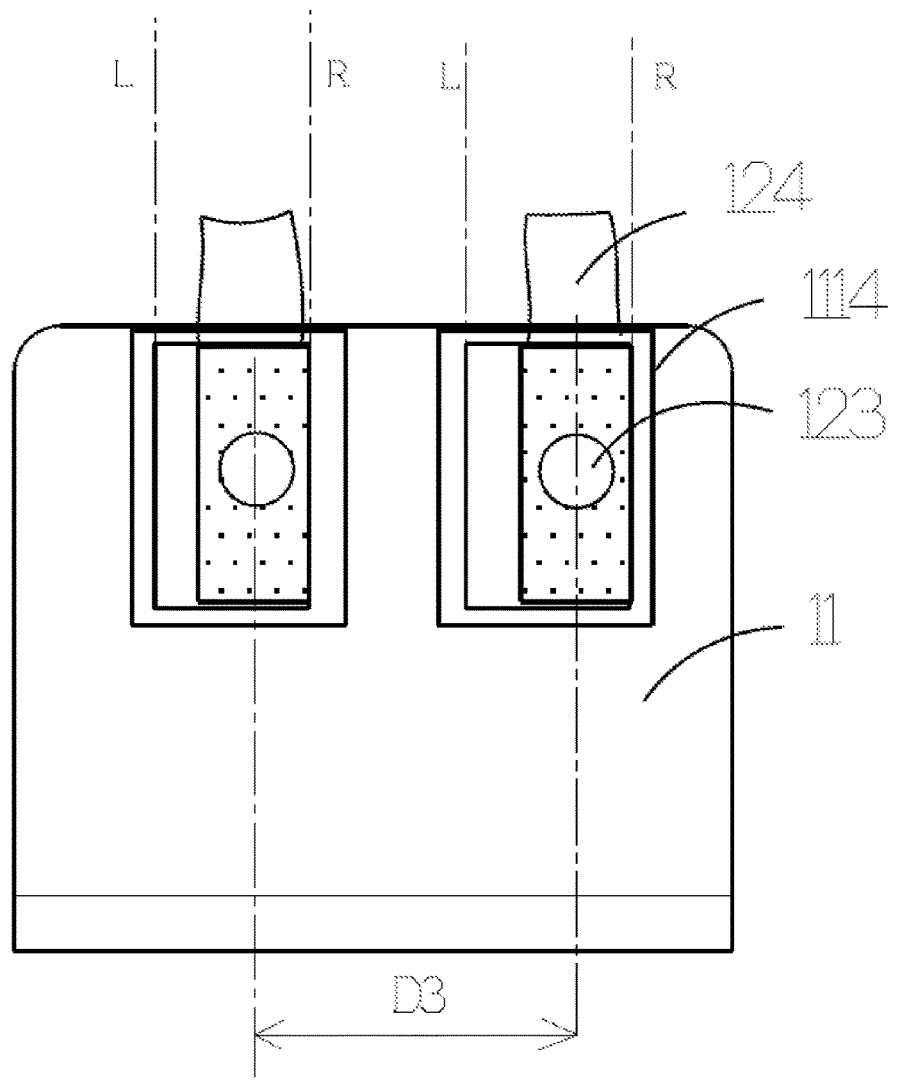
FIG. 15 is a top view showing the inflatable pillar in the fourth example of a hemostatic equipment according to the invention placed in a third mode.

The distance size between the left and right boundaries L, R of the implantation area is larger than the width size of the inflatable pillar 12, such that the location at which the inflatable pillar 12 be implanted onto the pallet 11 is not unique. As shown in FIG. 13, the implantation locations of the two inflatable pillars 12 on the pallet 11 are adjacent to the left and right boundaries L, R of the square-like implantation area, respectively. In such state, the center distance size length of the two inflatable pillars 12 is represented as symbol D1. As shown in FIG. 14, the implantation locations of the two inflatable pillars 12 on the pallet 11 are adjacent to the right and left boundaries R, L of the square-like implantation area, respectively. In such state, the center distance size length of the two inflatable pillars 12 is represented as symbol D2. As shown in FIG. 15, the implantation locations of the two inflatable pillars 12 on the pallet 11 are both adjacent to the right boundary R of the square-like implantation area. In such state, the center distance size length of the two inflatable pillars 12 is represented as symbol D3. Form what disclosed in FIGS. 13 to 15, the length represented as symbol D1 is larger than that represented as symbol D3, which is larger than the length represented as symbol D2. Therefore, the length of the center distance for the two inflatable pillars 12 in the example may be adjusted in adaptation to distance between two nostrils of a patient for applicability to patients with various somatotypes.

Additionally, in the example, the inflatable pillar 12 comprises a through-hole 123, which has openings on the head 121 and the body 122, respectively. Preferably, the through-hole 123 extends from the top surface of the head 121 to the bottom surface of the body 122. Correspondingly, the location of the carrier 111 facing the through-hole 123 is formed with a hole in communication with the through-hole 123. As such, the through-hole 123 of the inflatable pillar 12 and the hole of the carrier 111 may act as the channel for respiration of a patient, and may also act as channel for a medical staff to fill medicine in the inflatable pillar 12.

The hemostatic equipment 1 is provided with a test strip 124, which may contact the inflatable pillar 12 for testing the state of the inflatable pillar 12 through, for example, color change in order for a patient to handle the use state of the inflatable pillar 12. For example, the test strip 124 may be used to test the liquid absorption state of the inflatable pillar 12. More particularly, the test strip 124 may further test the composition of the liquid absorbed by the inflatable pillar 12 in order for medical care judgment.

FIFTH EXAMPLE

Figure 16:
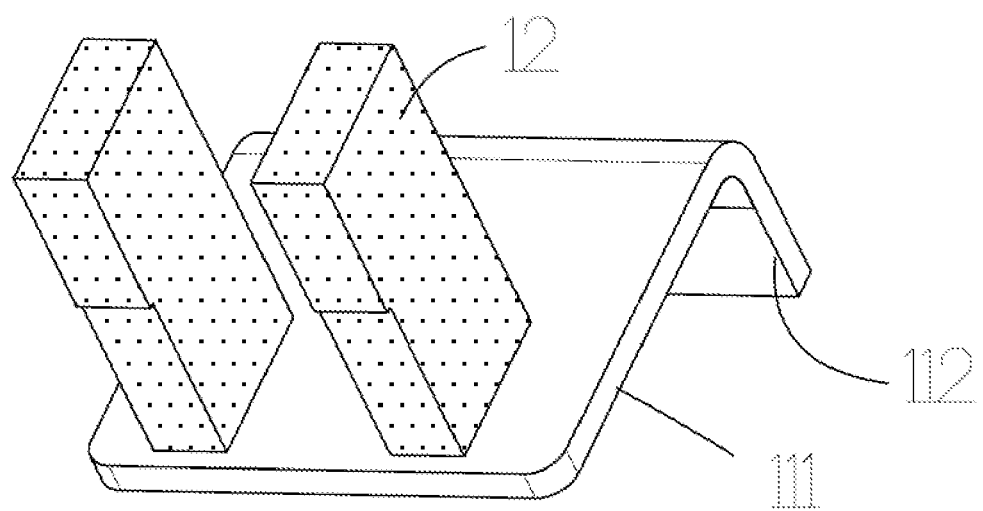
FIG. 16 is a schematic diagram showing a fifth example of a hemostatic equipment according to the invention.
Figure 17:
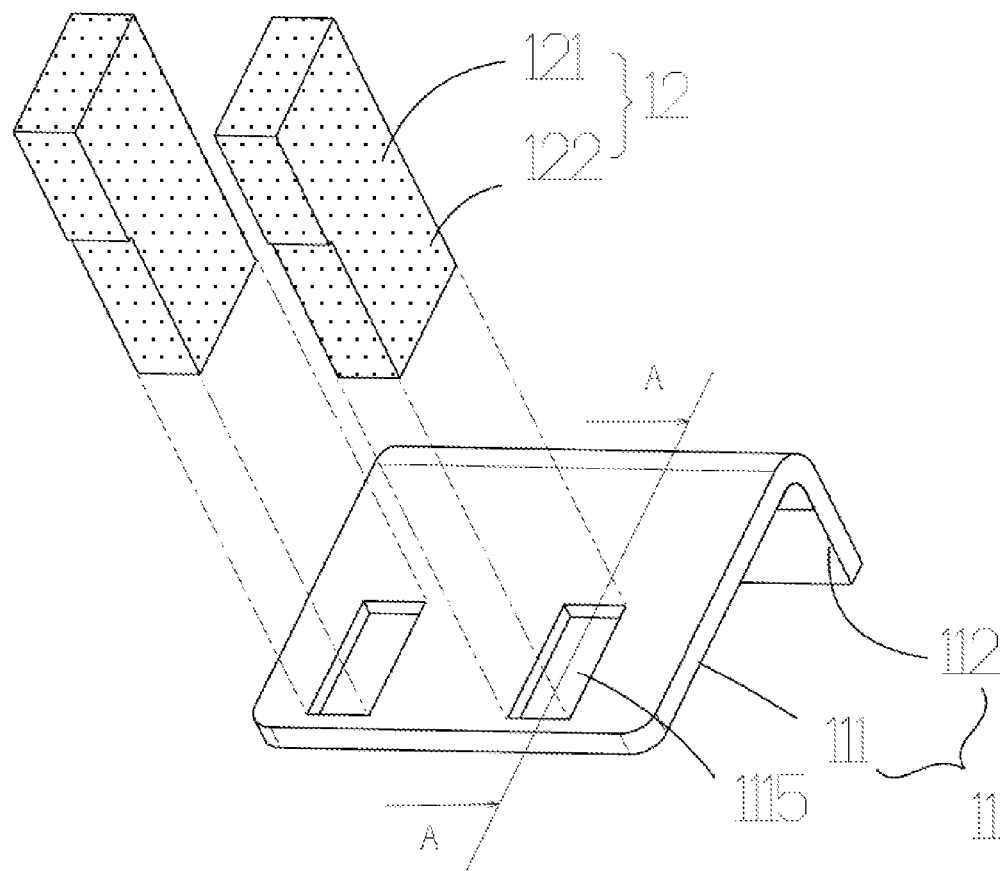
FIG. 17 is a breakdown drawing showing the hemostatic equipment shown in FIG. 16.
Figure 18:
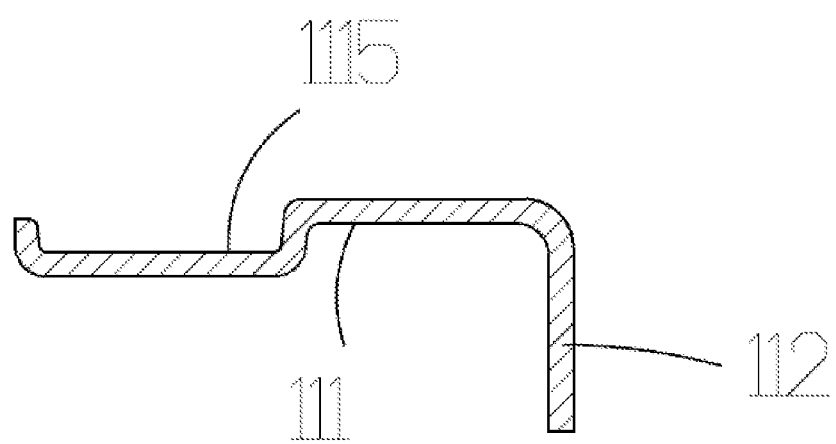
FIG. 18 is a profile drawing taken along AA line shown in FIG. 16.

Refer to FIGS. 16 to 18 showing schematic diagrams of the fifth example for the hemostatic equipment of the invention. As shown in FIG. 17, the location of the carrier 111 of the pallet 11 in the example for implanting the inflatable pillar 12 is provided concavely with a fixation pit 1115 in advance to replace the wall disclosed in the examples above. The fixation pit 1115 may be filled with adhesive for sticking and fixing the tail end of the body 122 of the inflatable pillar 12 entering the fixation pit 1115 to achieve implantation of the inflatable pillar 12 onto the carrier 111. In addition to the adhesive, other fixation mechanisms for the fixation pit 1115 may also be selected to fix the inflatable pillar 12 entering the fixation pit 1115.

SIXTH EXAMPLE

Figure 19:
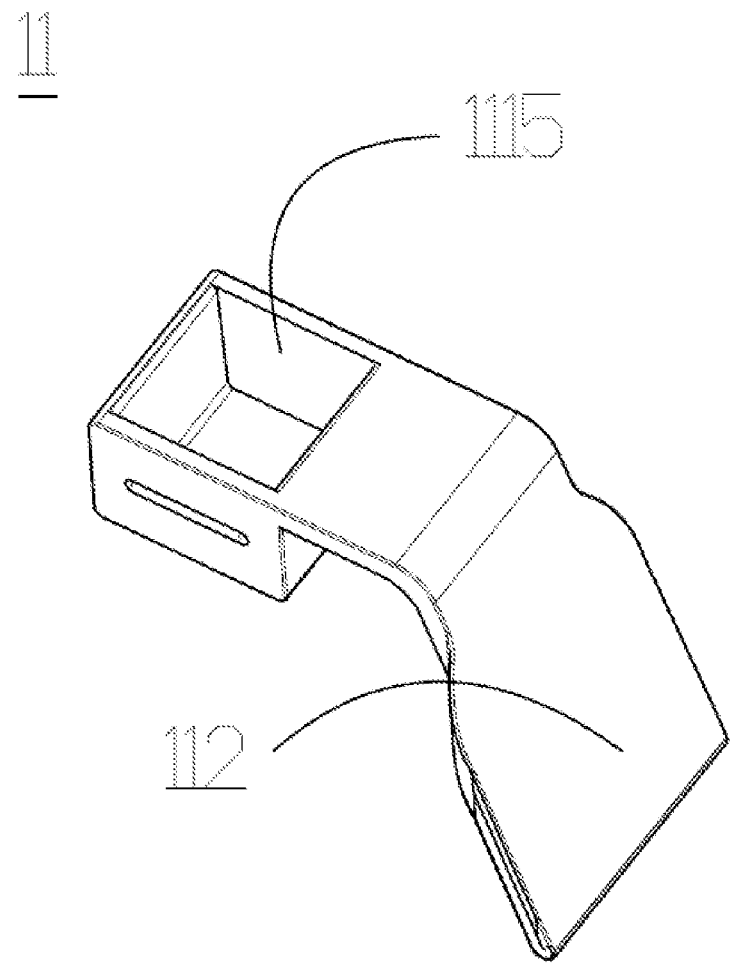
FIG. 19 is a schematic diagram showing a sixth example of a hemostatic equipment according to the invention.

Refer to FIG. 19 showing schematic diagrams of the sixth example for the hemostatic equipment of the invention. As shown in FIG. 19, the location of the carrier 111 of the pallet 11 in the example for implanting the inflatable pillar 12 is provided concavely with a fixation pit 1115 in advance to replace the wall disclosed in the examples above.

In summary, the hemostatic equipment of the invention comprises an inflatable pillar and a pallet. The head of the inflatable pillar is exposed with a pressing surface. The holder of the pallet is used for a patient to hold, while the applied force moves the carrier of the pallet toward to a nostril of a patient. Moreover, there is provided with foolproof effect for operation to ensure that the pressing surface of the head of the inflatable pillar may be in alignment with a bleeding site after entering a nasal cavity of a patient in order to stop bleeding inside a nasal cavity of a patient. As such, a patient can operate the hemostatic equipment by oneself without assistance from professional medical staff so that it is applicable to home use.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A hemostatic equipment for stopping bleeding in a nasal cavity of a patient, comprising:
   a pallet having a carrier and a holder extending downwards from a first end of said carrier; and
   at least one inflatable pillar having a head and a body attached to a second end of said carrier and said head being inserted into the nasal cavity of the patient to apply pressure on a bleeding site in the nasal cavity, and wherein said inflatable pillar is made of a foam material containing polyvinyl alcohol,
   wherein another inflatable pillar is provided so that said inflatable pillars can be respectively inserted into left and right nostrils of the patient; and
   wherein said second end of said carrier comprises a left cantilever and a right cantilever, and said inflatable pillars are arranged on said left cantilever and said right cantilever, respectively.

2. The hemostatic equipment according to claim 1, wherein said pallet is split for separating said left cantilever and said right cantilever.

3. The hemostatic equipment according to claim 1, wherein said opening of said carrier is formed along an area where said pallet can be split.

* * * * *